(12) United States Patent
Hattori et al.

(10) Patent No.: US 10,220,094 B2
(45) Date of Patent: Mar. 5, 2019

(54) AQUEOUS SOLUTION CONTAINING N-LONG-CHAIN ACYL ACIDIC AMINO ACID AND/OR SALT THEREOF, AND METHOD FOR PRODUCING SAME

(71) Applicant: AJINOMOTO CO., INC., Tokyo (JP)

(72) Inventors: Gaku Hattori, Kawasaki (JP); Hiroji Ishii, Kawasaki (JP); Masahiro Ino, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 15/139,600

(22) Filed: Apr. 27, 2016

(65) Prior Publication Data

US 2016/0235850 A1 Aug. 18, 2016

Related U.S. Application Data

(63) Continuation of application No. PCT/JP2014/078856, filed on Oct. 30, 2014.

(30) Foreign Application Priority Data

Oct. 31, 2013 (JP) ................. 2013-226965

(51) Int. Cl.
| | | |
|---|---|---|
| *A61K 8/44* | (2006.01) | |
| *A61K 47/18* | (2017.01) | |
| *A61Q 5/02* | (2006.01) | |
| *A61Q 19/10* | (2006.01) | |
| *C07C 231/02* | (2006.01) | |
| *C07C 233/47* | (2006.01) | |
| *C07C 233/49* | (2006.01) | |
| *C11D 1/10* | (2006.01) | |
| *C11D 17/04* | (2006.01) | |
| *B01F 17/00* | (2006.01) | |
| *C09K 15/20* | (2006.01) | |

(52) U.S. Cl.
CPC ............ *A61K 47/183* (2013.01); *A61K 8/44* (2013.01); *A61Q 5/02* (2013.01); *A61Q 19/10* (2013.01); *B01F 17/0042* (2013.01); *C07C 231/02* (2013.01); *C07C 233/47* (2013.01); *C07C 233/49* (2013.01); *C09K 15/20* (2013.01); *C11D 1/10* (2013.01); *C11D 17/041* (2013.01)

(58) Field of Classification Search
CPC .................................................. A61K 47/183

USPC .......................................................... 514/773
See application file for complete search history.

(56) References Cited

U.S. PATENT DOCUMENTS

| | | | |
|---|---|---|---|
| 5,534,199 A * | 7/1996 | Winkler, III ............. | C11D 1/94 134/42 |
| 5,854,199 A | 12/1998 | Oshimura et al. | |
| 6,008,390 A | 12/1999 | Hattori et al. | |
| 6,093,839 A | 7/2000 | Hingott et al. | |
| 2006/0239952 A1* | 10/2006 | Hattori .................... | A61K 8/361 424/70.14 |
| 2010/0273879 A1 | 10/2010 | Klug et al. | |

FOREIGN PATENT DOCUMENTS

| | | | |
|---|---|---|---|
| CN | 100448968 C | | 1/2009 |
| CN | 102126984 A | | 7/2011 |
| CN | 102863348 A | | 1/2013 |
| JP | 7-2747 A | | 1/1995 |
| JP | 07002747 | * | 1/1995 |
| JP | 10-81656 A | | 3/1998 |
| JP | 10-121091 A | | 5/1998 |
| JP | 11-286471 A | | 10/1999 |
| JP | 2001-247531 A | | 9/2001 |
| JP | 11-286471 | * | 1/2005 |
| JP | 2005-306751 A | * | 1/2005 |
| JP | WO 2005/033255 | * | 4/2005 |
| JP | 2005-306751 A | | 11/2005 |
| JP | 2005-325204 A | * | 11/2005 |
| JP | 2010-241909 A | | 10/2010 |
| JP | 2011-503218 A | | 1/2011 |
| WO | WO 2005/033255 A1 | | 4/2005 |

OTHER PUBLICATIONS

Combined Chinese Office Action and Search Report dated Nov. 28, 2016 in Patent Application No. 201480059821.0 (with English translation of categories of cited documents).
International Search Report dated Feb. 3, 2015 in PCT/JP2014/078856.

* cited by examiner

*Primary Examiner* — Nizal S Chandrakumar
(74) *Attorney, Agent, or Firm* — Oblon, McClelland, Maier & Neustadt, L.L.P.

(57) ABSTRACT

The present invention provides a method of producing an aqueous solution containing an $N$—$C_{8-22}$ acyl acidic amino acid and/or a salt thereof and having pH 8.4-9.5, including the first step for reacting an acidic amino acid and/or a salt thereof with a $C_{8-22}$ fatty acid chloride in a water solvent at pH 10-13 to form an $N$—$C_{8-22}$ acyl acidic amino acid salt, and the second step for adjusting the pH of the aqueous solution after the first step to 8.4-9.5.

5 Claims, No Drawings

AQUEOUS SOLUTION CONTAINING N-LONG-CHAIN ACYL ACIDIC AMINO ACID AND/OR SALT THEREOF, AND METHOD FOR PRODUCING SAME

CROSS REFERENCES TO RELATED APPLICATIONS

This application is a continuation of International Patent Application No. PCT/JP2014/078856, filed on Oct. 30, 2014, and claims priority to Japanese Patent Application No. 2013-226965, filed on Oct. 31, 2013, all of which are incorporated herein by reference in their entireties.

BACKGROUND OF THE INVENTION

Field of the Invention

The present invention relates to an aqueous solution containing an N-long chain acyl acidic amino acid (specifically an N—$C_{8-22}$ acyl acidic amino acid) and/or a salt thereof, and a production method thereof.

Discussion of the Background

Since N-long chain acyl acidic amino acid salt has a surface active action, a sterilizing action, a metal corrosion suppressive action and the like, it is useful as a starting material of detergents, dispersing agents, emulsifiers, antibacterial agents, preservatives and the like. Particularly, it is highly useful as a starting material of detergents such as shampoo, body shampoo and the like since it is mild to the skin.

As a method of synthesizing N-long chain acyl acidic amino acid (e.g., N-long chain acylglutamic acid) or a salt thereof, a method including condensing acidic amino acid (e.g., glutamic acid) or a salt thereof and long chain fatty acid chloride in a water solvent, or a mixed solvent of hydrophilic organic solvent such as acetone, t-butanol, propylene glycol and the like and water, in the presence of a base is known (Schotten-Baumann reaction, see, for example, patent document 1). In patent document 1, however, the obtained N-long chain acyl acidic amino acid is precipitated to recover same as a solid, and the utility of the aqueous solution per se after the reaction has not been evaluated.

In addition, N-long chain acyl acidic amino acid dipeptide is known as a substance that improves water resistance and creaky feeling of detergents containing N-long chain acyl acidic amino acid (patent document 2). However, N-long chain acyl acidic amino acid dipeptide needs to be obtained by acylating acidic amino acid dipeptide by the Schotten-Baumann reaction and the like, and is an expensive substance difficult to obtain.

DOCUMENT LIST

Patent Documents patent document 1: JP-A-10-81656
patent document 2: JP-A-10-121091

SUMMARY OF THE INVENTION

Problems to be Solved by the Invention

When an aqueous reaction solution containing N-long chain acyl amino acid and/or a salt thereof obtained by the Schotten-Baumann reaction of acidic amino acid and/or a salt thereof with long chain fatty acid chloride can be directly utilized as a detergent and the like or a starting material thereof, the production step and facility can be simplified by the omission of the recovery, washing and drying processes of the N-long chain acyl amino acid and/or a salt thereof, and a low environmental load type production process which is completely free from waste liquids can be achieved.

To handle the aforementioned aqueous reaction solution directly as a detergent and the like or a starting material thereof, the aqueous reaction solution is required to show stability to high temperature and low temperature. In addition, unreacted acidic amino acid and/or a salt thereof (e.g., glutamic acid, glutamate) present in the aqueous reaction solution are/is converted to lactam (e.g., pyroglutamic acid, pyroglutamate) due to an intramolecular condensation reaction under high temperature conditions. Also, there is a problem that the solubility of N-long chain acylglutamic acid and/or a salt thereof obtained by the Schotten-Baumann reaction decreases during the low temperature preservation of the aqueous reaction solution, thus resulting in precipitation.

The present invention has been made by taking note of the above-mentioned situation, and aims to provide an aqueous solution containing N-long chain acyl amino acid and/or a salt thereof having superior stability at high temperature and low temperature.

Means of Solving the Problems

The present inventors have conducted intensive studies in an attempt to achieve the above-mentioned object, and found that an aqueous solution containing N—$C_{8-22}$ acyl acidic amino acid and/or a salt thereof having superior stability at low temperature and high temperature can be obtained by reacting acidic amino acid and/or a salt thereof with $C_{8-22}$ fatty acid chloride in a water solvent at pH 10-13, and adjusting the pH of the aqueous reaction solution to fall within a certain range. The present invention based on the finding is as described below.

[1] A method of producing an aqueous solution comprising an N—$C_{8-22}$ acyl acidic amino acid and/or a salt thereof and having pH 8.4-9.5, comprising
 the first step for reacting an acidic amino acid and/or a salt thereof with a $C_{8-22}$ fatty acid chloride in a water solvent at pH 10-13 to form an N—$C_{8-22}$ acyl acidic amino acid and/or a salt thereof, and
 the second step for adjusting the pH of the aqueous solution after the first step to 8.4-9.5.
[2] The production method of the aforementioned [1], wherein the pH of the aqueous solution after the first step is adjusted to 8.6-9.2.
[3] The production method of the aforementioned [1] or [2], wherein the acidic amino acid and/or a salt thereof are/is one or more selected from glutamic acid, aspartic acid and salts thereof.
[4] The production method of the aforementioned [1] or [2], wherein the acidic amino acid and/or a salt thereof are/is glutamic acid and/or a sodium salt thereof.
[5] The production method of any one of the aforementioned [1]-[4], wherein the $C_{8-22}$ fatty acid chloride is one or more selected from octanoyl chloride, decanoyl chloride, lauroyl chloride, myristoyl chloride, palmitoyl chloride, and coconut oil fatty acid chloride.
[6] The production method of any one of the aforementioned [1]-[4], wherein the $C_{8-22}$ fatty acid chloride is lauroyl chloride and/or coconut oil fatty acid chloride.

[7] The production method of any one of the aforementioned [1]-[4], wherein the $C_{8-22}$ fatty acid chloride is coconut oil fatty acid chloride.

[8] The production method of any one of the aforementioned [1]-[7], wherein the reaction of the first step is performed in the presence of sodium hydroxide.

[9] The production method of any one of the aforementioned [1]-[8], further comprising a step for pressure filtration.

[10] The production method of any one of the aforementioned [1]-[9], wherein the water solvent does not contain a substantially hydrophilic organic solvent.

[11] The production method of any one of the aforementioned [1]-[10], wherein the aqueous solution after the second step comprises 1.0-10.0 wt % of the acidic amino acid and/or a salt thereof, and 10.0-30.0 wt % of the N—$C_{8-22}$ acyl acidic amino acid and/or a salt thereof.

[12] The production method of any one of the aforementioned [1]-[11], wherein the aqueous solution after the second step further comprises an N—$C_{8-22}$ acyl acidic amino acid dipeptide and/or a salt thereof.

[13] The production method of the aforementioned [12], wherein a content of the N—$C_{8-22}$ acyl acidic amino acid dipeptide and/or a salt thereof in the aqueous solution is 0.5-5.0 wt %.

[14] The production method of any one of the aforementioned [1]-[13], wherein the aqueous solution after the second step further comprises an N—$C_{8-22}$ acyl acidic amino acid tripeptide and/or a salt thereof.

[15] The production method of any one of the aforementioned [1]-[14], wherein the aqueous solution after the second step further comprises a $C_{8-22}$ fatty acid and/or a salt thereof.

[16] The production method of any one of the aforementioned [1]-[15], further comprising a step for packing the aqueous solution after the second step in a container.

[17] An aqueous solution comprising 1.0-10.0 wt % of an acidic amino acid and/or a salt thereof, 10.0-30.0 wt % of an N—$C_{8-22}$ acyl acidic amino acid and/or a salt thereof, and 0.5-5.0 wt % of an N—$C_{8-22}$ acyl acidic amino acid dipeptide and/or a salt thereof, and having pH 8.4-9.5.

[18] The aqueous solution of the aforementioned [17], wherein the pH is 8.6-9.2.

[19] The aqueous solution of the aforementioned [17] or [18], wherein the acidic amino acid and/or a salt thereof are/is one or more selected from glutamic acid, aspartic acid and sodium salts thereof.

[20] The aqueous solution of the aforementioned [17] or [18], wherein the acidic amino acid and/or a salt thereof are/is glutamic acid and/or a sodium salt thereof.

[21] The aqueous solution of any one of the aforementioned [17]-[20], wherein the N—$C_{8-22}$ acyl acidic amino acid and/or a salt thereof are/is one or more selected from N—$C_{8-22}$ acylglutamic acid, N—$C_{8-22}$ acylaspartic acid and sodium salts thereof.

[22] The aqueous solution of any one of the aforementioned [17]-[20], wherein the N—$C_{8-22}$ acyl acidic amino acid and/or a salt thereof are/is an N—$C_{8-22}$ acylglutamic acid and/or a sodium salt thereof.

[23] The aqueous solution of any one of the aforementioned [17]-[20], wherein the N—$C_{8-22}$ acyl acidic amino acid and/or a salt thereof are/is N-cocoylglutamic acid and/or a sodium salt thereof.

[24] The aqueous solution of any one of the aforementioned [17]-[23], wherein the N—$C_{8-22}$ acyl acidic amino acid dipeptide and/or a salt thereof are/is one or more selected from N—$C_{8-22}$ acylglutamyl-glutamic acid, N—$C_{8-22}$ acylaspartyl-glutamic acid, N—$C_{8-22}$ acylglutamyl-aspartic acid, N—$C_{8-22}$ acylaspartyl-aspartic acid, and sodium salts thereof.

[25] The aqueous solution of any one of the aforementioned [17]-[23], wherein the N—$C_{8-22}$ acyl acidic amino acid dipeptide and/or a salt thereof are/is an N—$C_{8-22}$ acylglutamyl-glutamic acid and/or a sodium salt thereof.

[26] The aqueous solution of any one of the aforementioned [17]-[23], wherein the N—$C_{8-22}$ acyl acidic amino acid dipeptide and/or a salt thereof are/is N-cocoylglutamyl-glutamic acid and/or a sodium salt thereof.

[27] The aqueous solution of any one of the aforementioned [17]-[26], further comprising an N—$C_{8-22}$ acyl acidic amino acid tripeptide and/or a salt thereof.

[28] The aqueous solution of the aforementioned [27], wherein the N—$C_{8-22}$ acyl acidic amino acid tripeptide and/or a salt thereof are/is one or more selected from N—$C_{8-22}$ acylglutamyl-glutamyl-glutamic acid, N—$C_{8-22}$ acylaspartyl-glutamyl-glutamic acid, N—$C_{8-22}$ acylglutamyl-aspartyl-glutamic acid, N—$C_{8-22}$ acylaspartyl-aspartyl-glutamic acid, N—$C_{8-22}$ acylaspartyl-aspartyl-aspartic acid, N—$C_{8-22}$ acylglutamyl-aspartyl-aspartic acid, N—$C_{8-22}$ acylaspartyl-glutamyl-aspartic acid, N—$C_{8-22}$ acylglutamyl-glutamyl-aspartic acid, and sodium salts thereof.

[29] The aqueous solution of the aforementioned [27], wherein the N—$C_{8-22}$ acyl acidic amino acid tripeptide and/or a salt thereof are/is an N—$C_{8-22}$ acylglutamyl-glutamyl-glutamic acid and/or a sodium salt thereof.

[30] The aqueous solution of the aforementioned [27], wherein the N—$C_{8-22}$ acyl acidic amino acid tripeptide and/or a salt thereof are/is N-cocoylglutamyl-glutamyl-glutamic acid and/or a sodium salt thereof.

[31] The aqueous solution of any one of the aforementioned [17]-[30], further comprising a $C_{8-22}$ fatty acid and/or a salt thereof.

[32] The aqueous solution of the aforementioned [31], wherein the $C_{8-22}$ fatty acid and/or a salt thereof are/is one or more selected from octanoic acid, decanoic acid, lauric acid, myristic acid, palmitic acid, coconut oil fatty acid, and sodium salts thereof.

[33] The aqueous solution of the aforementioned [31], wherein the $C_{8-22}$ fatty acid and/or a salt thereof are/is one or more selected from lauric acid, coconut oil fatty acid, and sodium salts thereof.

[34] The aqueous solution of the aforementioned [31], wherein the $C_{8-22}$ fatty acid and/or a salt thereof are/is coconut oil fatty acid and/or a sodium salt thereof.

[35] The aqueous solution of any one of the aforementioned [17]-[34], which is packed in a container.

Effect of the Invention

According to the present invention, an aqueous solution containing an N—$C_{8-22}$ acyl acidic amino acid and/or a salt thereof having superior stability at low temperature and high temperature is obtained.

DETAILED DESCRIPTION OF THE PREFERRED EMBODIMENTS

The production method of the present invention includes the first step for reacting an acidic amino acid and/or a salt thereof with a $C_{8-22}$ fatty acid chloride in a water solvent at pH 10-13 to form an N—$C_{8-22}$ acyl acidic amino acid and/or a salt thereof. The pH of the water solvent containing the reaction product in the first step (i.e., reaction system) is preferably 10.5-12.5, more preferably 11.0-12.0.

The acidic amino acid used in the first step is an amino acid having two or more carboxy groups. The acidic amino acid may be an optically active form or a racemate. The acidic amino acid is preferably monoaminodicarboxylic acid, more preferably glutamic acid and/or aspartic acid, more preferably glutamic acid. The glutamic acid and aspartic acid may be each an L form or D form, preferably an L form. Examples of the salt of the acidic amino acid include alkali metal salts such as sodium salt, potassium salt and the like; alkaline earth metal salts such as magnesium salt, calcium salt and the like; alkanolamine salts such as triethanolamine salt and the like; ammonium salt; choline salt; and salts with basic amino acid such as lysine salt, ornithine salt, arginine salt and the like. The salt is preferably an alkali metal salt, more preferably a sodium salt. Since acidic amino acid has two or more carboxy groups, all carboxy groups of a salt thereof may have a salt form (—COOM, M is counter cation), or only a part of the carboxy groups may have a salt form.

The "acidic amino acid and/or a salt thereof" to be used in the first step is/are preferably one or more selected from glutamic acid, aspartic acid and salts thereof, more preferably one or more selected from glutamic acid, aspartic acid, sodium salts thereof, and potassium salts thereof (i.e., one or more selected from glutamic acid, aspartic acid, monosodium glutamate, monopotassium glutamate, monosodium aspartate, monopotassium aspartate, glutamate disodium, dipotassium glutamate, disodium aspartate and dipotassium aspartate), further preferably one or more selected from glutamic acid, a sodium salt thereof, and potassium salts thereof (i.e., one or more selected from glutamic acid, glutamate monosodium, glutamate monopotassium, disodium glutamate and dipotassium glutamate), still further preferably glutamic acid and/or a sodium salt thereof (i.e., one or more selected from glutamic acid, monosodium glutamate and disodium glutamate), particularly preferably one or more selected from monosodium glutamate and disodiumglutamate, most preferably monosodium glutamate. These may be in the form of hydrates.

The $C_{8-22}$ fatty acid chloride to be used in the first step is fatty acid chloride having a carbon number of 8-22. The $C_{8-22}$ fatty acid chloride may be saturated or unsaturated. Examples of the $C_{8-22}$ fatty acid chloride include a fatty acid chloride having a single composition, such as octanoyl chloride, nonanoyl chloride, decanoyl chloride, undecanoyl chloride, lauroyl chloride, tridecanoyl chloride, myristoyl chloride, stearoyl chloride, palmitoyl chloride, behenoyl chloride, isostearoyl chloride, oleoyl chloride and the like; and mixed fatty acid chloride containing these, such as coconut oil fatty acid chloride, beef tallow fatty acid chloride, hydrogenated beef tallow fatty acid chloride, soybean oil fatty acid chloride, cottonseed oil fatty acid chloride, castor oil fatty acid chloride, olive oil fatty acid chloride, palm oil fatty acid chloride, palm kernel oil fatty acid chloride and the like. The $C_{8-22}$ fatty acid chloride is preferably octanoyl chloride, decanoyl chloride, lauroyl chloride, myristoyl chloride, palmitoyl chloride, or coconut oil fatty acid chloride, more preferably lauroyl chloride, or coconut oil fatty acid chloride, most preferably coconut oil fatty acid chloride.

The base used to maintain the pH of the reaction system in the first step at 10-13 is not particularly limited and includes, for example, sodium hydroxide, potassium hydroxide, calcium hydroxide, sodium carbonate, ammonia and the like. Of these, sodium hydroxide is preferable.

The N—$C_{8-22}$ acyl acidic amino acid formed in the first step is an acidic amino acid derivative wherein the hydrogen atom of the amino group is substituted by an acyl group having a carbon number of 8-22. The $C_{8-22}$ acyl group is specifically an acyl group corresponding to the $C_{8-22}$ fatty acid chloride to be used in the first step, from which chloride has been removed. Examples of the $C_{8-22}$ acyl group include an acyl group having a single composition, such as octanoyl group, nonanoyl group, decanoyl group, undecanoyl group, lauroyl group, tridecanoyl group, myristoyl group, stearoyl group, palmitoyl group, behenoyl group, isostearoyl group, oleoyl group and the like; as well as mixed fatty acid acyl groups containing these, such as coconut oil fatty acid acyl group (also called cocoyl group), beef tallow fatty acid acyl group, hydrogenated beef tallow fatty acid acyl group, soybean oil fatty acid acyl group, cottonseed oil fatty acid acyl group, castor oil fatty acid acyl group, olive oil fatty acid acyl group, palm oil fatty acid acyl group, palm kernel oil fatty acid acyl group and the like. The $C_{8-22}$ acyl group is preferably octanoyl group, decanoyl group, lauroyl group, myristoyl group, palmitoyl group, or cocoyl group, more preferably lauroyl group, or cocoyl group.

The N—$C_{8-22}$ acyl acidic amino acid is preferably N—$C_{8-22}$ acylglutamic acid and/or N—$C_{8-22}$ acylaspartic acid.

Examples of the salt of N—$C_{1-22}$ acyl acidic amino acid include alkali metal salts such as sodium salt, potassium salt and the like; alkaline earth metal salts such as magnesium salt, calcium salt and the like; alkanolamine salts such as triethanolamine salt and the like; ammonium salt; choline salt; and salts with basic amino acid such as lysine salt, ornithine salt, arginine salt and the like. This salt is preferably alkali metal salt, more preferably sodium salt.

In the first step, the amount of the acidic amino acid and/or a salt thereof to be used is, for example, 0.8-1.5 mol per 1 mol of the $C_{8-22}$ fatty acid chloride. To form the below-mentioned N—$C_{8-22}$ acyl acidic amino acid dipeptide and N—$C_{8-22}$ acyl acidic amino acid tripeptide, the aforementioned amount of use is preferably 0.9-1.4 mol, more preferably 1.0-1.3 mol, per 1 mol of the $C_8$ fatty acid chloride. When mixed fatty acid chloride such as coconut oil fatty acid chloride and the like is used as the $C_{8-22}$ fatty acid chloride, the molecular weight thereof can be calculated by the weight ratio of octanoyl chloride, decanoyl chloride, lauroyl chloride, myristoyl chloride, and palmitoyl chloride constituting the coconut oil fatty acid chloride.

In the first step, the initial concentration of the acidic amino acid and/or a salt thereof in the reaction system is preferably 20-50 wt %, more preferably 25-40 wt %, to perform an efficient reaction with acid chloride.

In the first step, the reaction is preferably performed by adding dropwise $C_{8-22}$ fatty acid chloride to a stirring water solvent containing acidic amino acid and/or a salt thereof. The time of dropwise addition of the total amount of the $C_{8-22}$ fatty acid chloride is preferably 30-600 min, more preferably 60-450 min, to perform an efficient reaction with acidic amino acid and/or a salt thereof, and the temperature of the reaction system at that time is preferably 0-50° C., more preferably 5-40° C.

The reaction temperature of the first step after addition of entire $C_{8-22}$ fatty acid chloride to the reaction system is preferably 10-50° C., more preferably 20-40° C., to complete the reaction of fatty acid chloride with acidic amino acid and a salt thereof, and the reaction time of the first step is preferably 10-600 min, more preferably 30-480 min.

The water solvent used in the first step is preferably substantially free of a hydrophilic organic solvent (e.g., acetone, t-butanol, propylene glycol etc.). The water solvent being substantially free of a hydrophilic organic solvent means that the content of the hydrophilic organic solvent in a water solvent is not more than 5 wt %, or the water solvent does not contain a hydrophilic organic solvent. The content of the hydrophilic organic solvent in a water solvent is more preferably not more than 4 wt %, more preferably not more than 3 wt %, particularly preferably not more than 2 wt %.

Since the water solvent is substantially free of a hydrophilic organic solvent, the contents of acidic amino acid and/or a salt thereof, N—$C_{8-22}$ acyl acidic amino acid and/or a salt thereof, N—$C_{8-22}$ acyl acidic amino acid dipeptide and/or a salt thereof, N acyl acidic amino acid tripeptide and/or a salt thereof in the aqueous solution obtained the production method of the present invention increase and an effect is obtained that foaming and the sense of use of the aqueous solution are improved. The N—$C_{8-22}$ acyl acidic amino acid dipeptide and the like are mentioned below. Since the water solvent does not substantially contain a hydrophilic organic solvent, advantages are obtained that an influence on the working environment and countermeasure to the Fire Defense Law and the like do not need to be considered.

The production method of the present invention includes the second step for adjusting the pH of the aqueous solution after the first step to 8.4-9.5. The pH is preferably 8.6-9.2.

The acid to be used for adjusting the pH of the aqueous solution in the second step is not particularly limited, and inorganic acids such as hydrochloric acid, hydrobromic acid, sulfuric acid, phosphoric acid and the like; organic acids such as carboxylic acid (e.g., acetic acid, citric acid), sulfonic acid and the like can be used. Of these, an inorganic acid is preferable, and hydrochloric acid is more preferable.

When an acid is added to the aqueous solution in the second step, the temperature of the aqueous solution is preferably adjusted to 0-50° C. for safety. The temperature may be adjusted by, for example, using a known cooler, or adding water at ambient temperature or cold water to the aqueous solution.

The production method of the present invention preferably further includes a step for pressure filtration (hereinafter to be abbreviated as "pressure filtration step"). The pressure filtration step may be performed after the first step or after the second step, or both after the first step and after the second step. To finally remove impurity in the obtained aqueous solution, a pressure filtration step is preferably performed after the second step.

The temperature of the aqueous solution during filtration is preferably 20-90° C., more preferably 40-80° C., to improve the work efficiency of the pressure filtration.

In the pressure filtration step, a filter aid is preferably used. Examples of the filter aid include Celite (registered trade mark) and the like. The amount of a filter aid to be used is preferably 0.05-10 g, more preferably 0.1-5 g, per 100 g of the aqueous solution to improve the work efficiency of the pressure filtration.

After addition of a filter aid, an aqueous solution containing the filter aid is preferably agitated for a given time to allow for sufficient adsorption of the impurity to the filter aid. The agitation time is preferably 5-300 min, more preferably 10-200 min, and the temperature of the aqueous solution at that time is preferably 20-90° C., more preferably 40-80° C.

The pressure of the pressure filtration is preferably 0.2-10 MPa, more preferably 0.3-5 MPa, and the temperature of the aqueous solution at that time is preferably 20-90° C., more preferably 40-80° C. The pressure filtration can be performed using a known apparatus such as a stainless steel holder equipped with a tank and the like.

Surprisingly, the production method of the present invention can form not only N—$C_{8-22}$ acyl acidic amino acid and/or a salt thereof but also N—$C_{8-22}$ acyl acidic amino acid dipeptide and/or a salt thereof generally synthesized by acylation of acidic amino acid dipeptide and/or a salt thereof. The production method of the present invention can further form N—$C_{8-22}$ acyl acidic amino acid tripeptide and/or a salt thereof. As used herein, N—$C_{8-22}$ acyl acidic amino acid dipeptide is a derivative of dipeptide formed from acidic amino acid and refers to such derivative wherein the hydrogen atom of the amino group is substituted by an acyl group having a carbon number of 8-22. The N—$C_{8-22}$ acyl acidic amino acid tripeptide is a derivative of tripeptide formed from acidic amino acid and refers to such derivative wherein the hydrogen atom of the amino group is substituted by an acyl group having a carbon number of 8-22.

The N—$C_{8-22}$ acyl acidic amino acid dipeptide is preferably The N—$C_{8-22}$ one or more selected from N—$C_{8-22}$ acyl Glu-Glu, N—$C_{8-22}$ acyl Asp-Glu, N—$C_{8-22}$ acyl Glu-Asp and N—$C_{8-22}$ acyl Asp-Asp, more preferably, one or more selected from N—$C_{8-22}$ acyl Glu-Glu and N—$C_{8-22}$ acyl Asp-Asp, further preferably N—$C_{8-22}$ acyl Glu-Glu. When peptides are indicated by abbreviations in the present specification, each indication is based on the abbreviation conventionally used in the field of peptide. For example, "N—$C_{8-22}$ acyl Glu-Glu" shows "N—$C_{8-22}$ acylglutamyl-glutamic acid", and "N—$C_{8-22}$ acyl Asp-Asp" shows "N—$C_{8-22}$ acylaspartyl-aspartic acid".

Examples of the $C_{8-22}$ acyl group include an acyl group having a single composition, such as octanoyl group, nonanoyl group, decanoyl group, undecanoyl group, lauroyl group, tridecanoyl group, myristoyl group, stearoyl group, palmitoyl group, behenoyl group, isostearoyl group, oleoyl group and the like; and mixed fatty acid acyl groups containing these, such as coconut oil fatty acid acyl group (also called cocoyl group), beef tallow fatty acid acyl group, hydrogenated beef tallow fatty acid acyl group, soybean oil fatty acid acyl group, cottonseed oil fatty acid acyl group, castor oil fatty acid acyl group, olive oil fatty acid acyl group, palm oil fatty acid acyl group, palm kernel oil fatty acid acyl group and the like. The $C_{8-22}$ acyl group is preferably octanoyl group, decanoyl group, lauroyl group, myristoyl group, palmitoyl group, or cocoyl group, more preferably lauroyl group, or cocoyl group.

Examples of the salt of N—$C_{8-22}$ acyl acidic amino acid dipeptide include alkali metal salts such as sodium salt, potassium salt and the like; alkaline earth metal salts such as magnesium salt, calcium salt and the like; alkanolamine salts such as triethanolamine salt and the like; ammonium salt; choline salt; and salts with basic amino acid such as lysine salt, ornithine salt, arginine salt and the like. The salt is preferably alkali metal salt, more preferably sodium salt.

The N—$C_{8-22}$ acyl acidic amino acid tripeptide is preferably one or more selected from N—$C_{8-22}$ acyl Glu-Glu-Glu, N—$C_{8-22}$ acyl Asp-Glu-Glu, N—$C_{8-22}$ acyl Glu-Asp-Glu, N—$C_{8-22}$ acyl Asp-Asp-Glu, N—$C_{8-22}$ acyl Asp-Asp-Asp, N—$C_{8-22}$ acyl Glu-Asp-Asp, N—$C_{8-22}$ acyl Asp-Glu-Asp and N—$C_{8-22}$ acyl Glu-Glu-Asp, more preferably one or more selected from N—$C_{8-22}$ acyl Glu-Glu-Glu and N—$C_{8-22}$ acyl Asp-Asp-Asp, further preferably N—$C_{8-22}$ acyl Glu-Glu-Glu.

Examples of the $C_{8-22}$ acyl group include acyl groups having a single composition, such as octanoyl group, nonanoyl group, decanoyl group, undecanoyl group, lauroyl group, tridecanoyl group, myristoyl group, stearoyl group, palmitoyl group, behenoyl group, isostearoyl group, oleoyl group and the like; and mixed fatty acid acyl groups containing these, such as coconut oil fatty acid acyl group (also called cocoyl group), beef tallow fatty acid acyl group, hydrogenated beef tallow fatty acid acyl group, soybean oil fatty acid acyl group, cottonseed oil fatty acid acyl group, castor oil fatty acid acyl group, olive oil fatty acid acyl group, palm oil fatty acid acyl group, palm kernel oil fatty acid acyl group and the like. The $C_{8-22}$ acyl group is preferably octanoyl group, decanoyl group, lauroyl group, myristoyl group, palmitoyl group, or cocoyl group, more preferably lauroyl group, or cocoyl group.

Examples of the salt of N—$C_{8-22}$ acyl acidic amino acid tripeptide include alkali metal salts such as sodium salt, potassium salt and the like; alkaline earth metal salts such as magnesium salt, calcium salt and the like; alkanolamine salts such as triethanolamine salt and the like; ammonium salt; choline salt; and salts with basic amino acid such as lysine salt, ornithine salt, arginine salt and the like. The salt is preferably alkali metal salt, more preferably sodium salt.

The aqueous solution obtained by the production method of the present invention preferably contains not only N—$C_{8-22}$ acyl acidic amino acid and/or a salt thereof formed by the Schotten-Baumann reaction in the first step, but also acidic amino acid and/or a salt thereof which are/is unreacted starting material(s) thereof. The presence of the acidic amino acid and/or a salt thereof affords an effect that foaming and the sense of use are improved. The acidic amino acid and/or a salt thereof to be contained in the aqueous solution are/is the same as those/that explained above.

The aqueous solution obtained by the production method of the present invention preferably contains $C_{8-22}$ fatty acid and/or a salt thereof. Depending on the $C_{8-22}$ fatty acid and/or a salt thereof, an effect can be obtained that foaming and the sense of use are improved. The $C_{8-22}$ fatty acid is derived from $C_{8-22}$ fatty acid chloride used in the first step, and examples thereof include fatty acid having a single composition, such as octanoic acid, nonanoic acid, decanoic acid, undecanoic acid, lauric acid, tridecanoic acid, myristic acid, stearic acid, palmitic acid, behenic acid, isostearic acid, oleic acid and the like; and mixed fatty acid containing these, such as coconut oil fatty acid, beef tallow fatty acid, hydrogenated beef tallow fatty acid, soybean oil fatty acid, cottonseed oil fatty acid, castor oil fatty acid, olive oil fatty acid, palm oil fatty acid, palm kernel oil fatty acid and the like. The $C_{8-22}$ fatty acid is preferably octanoic acid, decanoic acid, lauric acid, myristic acid, palmitic acid, or coconut oil fatty acid, more preferably lauric acid, or coconut oil fatty acid, most preferably coconut oil fatty acid.

Examples of the salt of $C_{8-22}$ fatty acid include alkali metal salts such as sodium salt, potassium salt and the like; alkaline earth metal salts such as magnesium salt, calcium salt and the like; alkanolamine salts such as triethanolamine salt and the like; ammonium salt; choline salt; and salts with basic amino acid such as lysine salt, ornithine salt, arginine salt and the like. The salt is preferably alkali metal salt, more preferably sodium salt.

The content of acidic amino acid and/or a salt thereof in the aqueous solution obtained by the production method of the present invention is preferably 1.0-10.0 wt %, more preferably 2.0-8.0 mass %, the content of N—$C_{8-22}$ acyl acidic amino acid and/or a salt thereof is preferably 10.0-30.0 wt %, more preferably 15.0-25.0 mass %, and the content of N—$C_{8-22}$ acyl acidic amino acid dipeptide and/or a salt thereof is preferably 0.5-5.0 wt %, more preferably 1.0-4.0 mass %. When the content of each component is within the aforementioned preferable range, foaming and the sense of use of the obtained aqueous solution are improved. When both acidic amino acid and a salt thereof are present, the aforementioned content is the total amount thereof. The same applies to other contents.

The production method of the present invention preferably further includes a step for packing the aqueous solution after the second step in a container. The container is not particularly limited and, for example, any of bottle, can, bag and the like can be used. The material of the container is not particularly limited, and any of glass, plastic, metal, and a composite material of these can be used.

The present invention provides an aqueous solution comprising 1.0-10.0 wt % of acidic amino acid and/or a salt thereof, 10.0-30.0 wt % of N—$C_{8-22}$ acyl acidic amino acid and/or a salt thereof, and 0.5-5.0 wt % of N—$C_{8-22}$ acyl acidic amino acid dipeptide and/or a salt thereof, which has pH 8.4-9.5 and is obtained by the aforementioned method. The aqueous solution of the present invention may further contain N—$C_{8-22}$ acyl acidic amino acid tripeptide and/or a salt thereof. The aqueous solution of the present invention may further contain $C_{8-22}$ fatty acid and/or a salt thereof. The explanation (preferable specific examples, content etc.) of the components to be contained in the aqueous solution of the present invention, and the explanation of the containers in which the aqueous solution of the present invention is packed are as described above.

The aqueous solution of the present invention is superior in the stability at low temperature and high temperature, shows good foaming and sense of use, and is useful as a detergent, a dispersing agent, an emulsifier, an antibacterial agent, a preservative or the like; or a starting material thereof.

EXAMPLES

While the present invention is explained in more detail in the following by referring to Examples, it is not limited by the following Examples. It is of course possible to modify the present invention as long as it is compatible to the above-mentioned and the below-mentioned gist and practice the present invention, all of which are encompassed in the technical scope of the present invention.

In the following Examples, "%" means "wt %" unless particularly indicated otherwise.

Example 1

Production of Aqueous Solution Containing Sodium Salt of N-Cocoylglutamic Acid

Monosodium L-glutamate monohydrate (187 g, 1.00 mol) was suspended in water (300 mL), to which 48% aqueous sodium hydroxide solution (78 g) was added to prepare an aqueous solution (pH 12.0), and the solution was cooled to 15° C. Thereto were simultaneously added dropwise coconut oil fatty acid chloride (200 g, molecular weight calculated from the weight ratio of components: 219, 0.91 mol) and 48% aqueous sodium hydroxide solution (98 g) over 1 hr while maintaining the pH of the reaction system at 12.0 and the temperature at 15° C. After the completion of the dropwise addition, the temperature of the reaction system was raised to 30° C., and stirring was continued for 3 hr to complete the reaction. To the aqueous reaction solution were added water (320 mL) at ambient temperature and 35% hydrochloric acid (25 g) to adjust the pH to 9.0. To the aqueous solution was added celite (registered trade mark) (Product type: 577 LC) (6.0 g), and the mixture was heated to 70° C. and stirred at this temperature for 1 hr. The aqueous solution containing celite was filtered with pressure by using a stainless steel holder equipped with a tank (manufactured by ADVANTEC) at 70° C. and 0.4 MPa to give an aqueous solution (1180 g) containing sodium salt of N-cocoylglutamic acid. The composition of the obtained aqueous solution was examined by HPLC and ion chromatography under the following conditions. The results thereof are shown in Table 1.

(HPLC Analysis Conditions)
(1) Analyses of Sodium Salt of N-Cocoylglutamic Acid, Sodium Salt of Coconut Oil Fatty Acid, Sodium Salt of N-Cocoylglutamyl-Glutamic Acid, and Sodium Salt of N-Cocoylglutamyl-Glutamyl-Glutamic Acid
  instrument used: CLASS-LC20 series manufactured by Shimadzu Corporation
  detection UV: 210 nm
  column: YMC-Pack ODS-A 150×6.0 mmI.D., S-5 µm, 12 nm (product number: AA12S05-1506WT) manufactured by YMC CO., LTD.
  column temperature: 40° C.
  eluent: MeOH/phosphate buffer=71.5/28.5 (volume ratio) (phosphate buffer: 0.03 mol/L aqueous $NaH_2PO_4$ solution adjusted to pH 3.0 by adding $H_3PO_4$)
  flow rate: 1.2 mL/min
  measurement time: 90 min
  injection volume: 10 µL
(2) Analysis of Sodium Salt of Glutamic Acid
  instrument used: CLASS-LC20 series manufactured by Shimadzu Corporation
  detection UV: 210 nm
  column: YMC-Pack ODS-A 150×6.0 mmI.D., S-5 µm, nm (product number: AA12S05-1506WT) manufactured by YMC CO., LTD.
  column temperature: 40° C.
  eluent: MeOH/phosphate buffer=5/95 (volume ratio) (phosphate buffer: 0.05 mol/L aqueous $NaH_2PO_4$ solution adjusted to pH 2.5 by adding $H_3PO_4$, and added with octanesulfonic acid to 0.005 mol/L)
  flow rate: 1.0 mL/min
  measurement time: 60 min
  injection volume: 20
(Analysis Conditions of Ion Chromatography)
  analysis of sodium chloride
  instrument used: DX-100 manufactured by DIO NEX
  detection: electric conductivity detection
  column: IonPac AS11-HC 2 mm (10-32) manufactured by DIO NEX
  column temperature: 40° C.
  eluent: 0.1 M aqueous sodium hydroxide solution
  flow rate: 1.0 mL/min
  measurement time: 60 min
  injection volume: 20 µL

TABLE 1 composition of obtained aqueous solution

| component | content |
| --- | --- |
| water | 64-65% |
| sodium salt* of N-cocoylglutamic acid | 18-19% |
| sodium salt* of coconut oil fatty acid | 4-5% |
| sodium salt* of N-cocoylglutamyl-glutamic acid (sodium salt of N-cocoylglutamic acid dipeptide) | 2-3% |
| sodium chloride | 5-6% |
| sodium salt* of glutamic acid | 4-5% |

TABLE 1-continued composition of obtained aqueous solution

| component | content |
| --- | --- |
| sodium salt* of N-cocoylglutamyl-glutamyl-glutamic acid (sodium salt of N-cocoylglutamic acid tripeptide) | unknown** |

*Neutralization degree of each sodium salt is unknown.
**While the presence of sodium salt of N-cocoylglutamyl-glutamyl-glutamic acid could be confirmed, the content thereof could not be quantified.

(1) Low Temperature Preservation Test (Appearance of Aqueous Solution
  To the aqueous solution produced in Example 1 was added 48% aqueous sodium hydroxide solution or 35% hydrochloric acid to give an aqueous solution having pH 7.5-10.5. Each aqueous solution having a different pH was placed in a 50 mL sample tube, and preserved in a storage at −5° C. for 14 days. After preservation, each aqueous solution was taken out from the storage, the appearance thereof was visually observed over time, and evaluated by the following criteria. The results are shown in Table 2.
(Evaluation Criteria)
  ⊙: clear
  ◯: thin white turbidity, clear after temperature rise to room temperature
  Δ: strong white turbidity, clear after temperature rise to room temperature
  x: strong white turbidity, white turbidity even after temperature rise to room temperature
(2) High Temperature Preservation Test 1 (Content Change of Sodium Salt of Glutamic Acid)
  To the aqueous solution produced in Example 1 was added 48% aqueous sodium hydroxide solution or 35% hydrochloric acid to give an aqueous solution having pH 7.5-10.5. The content ($G_0$) of sodium salt of glutamic acid in each aqueous solution having different pH before preservation at a high temperature was measured by HPLC under the following conditions.
(Measurement Conditions of HPLC)
  instrument used: CLASS-LC20 series manufactured by Shimadzu Corporation
  detection: UV-210 nm
  column: YMC-PackODS-A 150×6.0 mmI.D., S-5 µm, 12 nm (product number: AA12S05-1506WT) manufactured by YMC CO., LTD.
  column temperature 40° C.
  eluent: MeOH/phosphate buffer=5/95
  (phosphate buffer: 0.05 mol/L aqueous $NaH_2PO_4$ solution adjusted to pH2.5 by adding $H_3PO_4$, and added with octanesulfonic acid to 0.005 mol/L)
  flow rate: 1.0 mL/min
  measurement time: 60 min
  injection volume: 20 µL,
  Then, each aqueous solution was placed in a 50 mL sample tube, and preserved in a storage at 70° C. for 14 days. After preservation, each aqueous solution was taken out from the storage, the content (G) of sodium salt of glutamic acid was measured by HPLC under the above-mentioned conditions, and evaluated by the following criteria. The results are shown in Table 2.
(Evaluation Criteria)
  ⊙: $G/G_0$ not less than 0.7
  ◯: $G/G_0$ not less than 0.5 and less than 0.7
  Δ: $G/G_0$ not less than 0.3 and less than 0.5
  x: $G/G_0$ less than 0.3

(3) High Temperature Preservation Test 2 (Permeability of Aqueous Solution)

To the aqueous solution produced in Example 1 was added 48% aqueous sodium hydroxide solution or 35% hydrochloric acid to give an aqueous solution having pH 7.5-10.5. Each aqueous solution having different pH was placed in a 50 mL sample tube, and preserved in a storage at 70° C. for 14 days. After the preservation, each aqueous solution was taken out from the storage, and the permeability of the aqueous solution was measured by ultraviolet visible spectrophotometer (N-570) manufactured by JASCO Corporation and evaluated according to the following criteria. The results are shown in Table 2.

(Evaluation Criteria)
⊙: permeability not less than 97%
◯: permeability not less than 95% and less than 97%
Δ: permeability not less than 93% and less than 95%
x: permeability less than 93%

TABLE 2

| | pH of aqueous solution | | | | | | | | | |
|---|---|---|---|---|---|---|---|---|---|---|
| | 7.5 | 8.0 | 8.2 | 8.4 | 8.6 | 8.8 | 9.0 | 9.2 | 9.5 | 10.0 | 10.5 |
| appearance of aqueous solution after low temperature preservation | X | Δ | Δ | Δ | ◯ | ⊙ | ⊙ | ⊙ | ⊙ | ⊙ | ⊙ |
| content change of sodium salt of glutamic acid after preservation at high temperature | ⊙ | ⊙ | ⊙ | ⊙ | ⊙ | ⊙ | ⊙ | ◯ | Δ | X | X |
| permeability of aqueous solution after preservation at high temperature | X | X | X | Δ | ◯ | ◯ | ⊙ | ⊙ | ⊙ | ⊙ | ⊙ | low temperature preservation: at −5° C. for 14 days
high temperature preservation: at 70° C. for 14 days From the results shown in Table 2, it is clear that an aqueous solution containing sodium salt of N-cocoylglutamic acid and having pH 8.4-9.5 (particularly pH 8.6-9.2) is superior in stability at low temperature and high temperature.

(4) Foaming Test

The aqueous solution produced in Example 1 (2.0 g) was diluted with tap water to 100 g (active agent concentration 0.5%), immersed in a water bath at 35° C. for 5 min, and the solution was foamed with a hand mixer (manufactured by Kai Corporation) for 10 sec. The volume of the foam was measured immediately thereafter and 2 min later. In addition, fineness of the foam was visually observed, and evaluated according to the following criteria. The results are shown in Table 3.

(Evaluation Criteria of Foam Quality)
⊙: foam is very fine
◯: foam is fine
Δ: foam is rough
x: foam is very rough As a Comparative Example, 0.5 wt % of N-cocoylglutamic acid prepared by the method described in patent document 1 based on monosodium salt was suspended in water, and then the aqueous solution was adjusted to pH 9.0 with 48% aqueous sodium hydroxide solution. Using the solution, a similar foaming test was performed. The results are shown in Table 3.

TABLE 3

| | Example 1 | | Comparative Example | |
|---|---|---|---|---|
| | immediately after | 2 min later | immediately after | 2 min later |
| foam volume (mL) | 180 | 140 | 100 | 60 |
| foam quality | ⊙ | ◯ | Δ | X |

From the results of Table 3, it is clear that the aqueous solution produced in Example 1 is superior in foaming and the sense of use as a detergent.

INDUSTRIAL APPLICABILITY

According to the present invention, an aqueous solution containing an N—$C_{8-22}$ acyl acidic amino acid and/or a salt thereof and having superior stability at low temperature and high temperature can be obtained. The aqueous solution is useful as a detergent, a dispersing agent, an emulsifier, an antibacterial agent, a preservative or the like; or a starting material thereof.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the m appended claims, the invention may be practiced otherwise than as specifically described herein.

All patents and other references mentioned above are incorporated in full herein by this reference, the same as if set forth at length.

The invention claimed is:
1. A detergent comprising an aqueous solution, wherein said aqueous solution comprises:
(A) 1.0 to 10.0 wt % of at least one member selected from the group consisting of an acidic amino acid and a salt of an acidic amino acid:
(B) 10.0 to 30.0 wt % of at least one member selected from the group consisting of an N—$C_{8-22}$ acyl acidic amino acid and a salt of an N—$C_{8-22}$ acyl acidic amino acid; and
(C) 0.5 to 5.0 wt % of at least one member selected from the group consisting of an N—$C_{8-22}$ acyl acidic amino acid dipeptide and a salt of an N—$C_{8-22}$ acyl acidic amino acid dipeptide, and
said aqueous solution has pH of 8.4 to 9.5.
2. The detergent according to claim 1, wherein said aqueous solution further comprises at least one member selected from the group consisting of an N—$C_{8-22}$ acyl acidic amino acid tripeptide and a salt of an N—$C_{8-22}$ acyl acidic amino acid tripeptide.
3. The detergent or starting material thereof according to claim 1, wherein said aqueous solution further comprises at least one member selected from the group consisting of a $C_{8-22}$ fatty acid and a salt of a $C_{8-22}$ fatty acid.

4. The detergent according to claim 2, wherein said aqueous solution further comprises at least one member selected from the group consisting of a $C_{8-22}$ fatty acid and a salt of a $C_{8-22}$ fatty acid.

5. The detergent according to claim 1, wherein said aqueous solution is substantially free of a hydrophilic organic solvent.

* * * * *

UNITED STATES PATENT AND TRADEMARK OFFICE
CERTIFICATE OF CORRECTION

PATENT NO. : 10,220,094 B2
APPLICATION NO. : 15/139600
DATED : March 5, 2019
INVENTOR(S) : Gaku Hattori et al.

Page 1 of 1

It is certified that error appears in the above-identified patent and that said Letters Patent is hereby corrected as shown below:

In the Claims

In Claim 3, Column 14, Line 64, "The detergent or starting material thereof according to" should read --The detergent according to--.

Signed and Sealed this
Twenty-sixth Day of November, 2019

Andrei Iancu
*Director of the United States Patent and Trademark Office*